(12) United States Patent
Ghorashi et al.

(10) Patent No.: US 8,640,537 B2
(45) Date of Patent: Feb. 4, 2014

(54) DUAL OPPOSING FIBER BRUSHING

(75) Inventors: Hossein M. Ghorashi, Knoxville, TN (US); James T. Wender, Seymour, TN (US); C. Roger Riley, Knoxville, TN (US)

(73) Assignee: Uster Technologies, AG, Uster (CH)

( * ) Notice: Subject to any disclaimer, the term of this patent is extended or adjusted under 35 U.S.C. 154(b) by 319 days.

(21) Appl. No.: 13/234,262

(22) Filed: Sep. 16, 2011

(65) Prior Publication Data
US 2013/0068009 A1   Mar. 21, 2013

(51) Int. Cl.
*G01L 5/04* (2006.01)
*D01G 19/00* (2006.01)

(52) U.S. Cl.
USPC .......................................... 73/159; 19/115 R

(58) Field of Classification Search
USPC .................................. 73/159; 19/115 R, 215
See application file for complete search history.

(56) References Cited

U.S. PATENT DOCUMENTS

| | | | | |
|---|---|---|---|---|
| 1,402,724 A | * | 1/1922 | Stukenborg | ..................... 56/13.2 |
| 2,373,768 A | * | 4/1945 | McCreery | ..................... 19/66 R |
| 2,438,393 A | * | 3/1948 | James et al. | ..................... 56/49 |
| 2,513,298 A | | 7/1950 | Fairbairn | |
| 3,057,019 A | | 10/1962 | Hertel | |
| 4,391,153 A | | 7/1983 | Taylor | |
| 5,907,394 A | | 5/1999 | Ghorashi | |
| 6,085,584 A | * | 7/2000 | Ramachandran et al. | ...... 73/159 |
| 2002/0157164 A1 | | 10/2002 | Shofner | |

FOREIGN PATENT DOCUMENTS

GB    621900    4/1949

OTHER PUBLICATIONS

"The Ashford 2 speed drum carder," pp. 1-6, XP55042148, Retrieved from the Internet: www.ashford.co.nz/newsite/pdfs_assembly_guides/ADCFADCC_web_84.pdf, (Jun. 16, 2008).

* cited by examiner

*Primary Examiner* — Hezron E Williams
*Assistant Examiner* — Nathaniel Kolb
(74) *Attorney, Agent, or Firm* — Luedeka Neely Group, P.C.; Rick Barnes

(57) ABSTRACT

A fiber sample conditioning system having a comb for engaging and retaining fibers to form a beard, and at least two rotating brushes for brushing the fibers simultaneously from opposite sides of the beard in a direction along the fibers away from the comb.

12 Claims, 3 Drawing Sheets

DUAL OPPOSING FIBER BRUSHING

FIELD

This invention relates to the field of fiber conditioning. More particularly, this invention relates to brushing cotton fibers prior to length and strength testing.

INTRODUCTION

Natural and man-made fibers are used for a variety of purposes. Such fibers are typically graded according to their properties, such as length and strength. For staple fibers, length and strength are typically measured by forming a fiber sample, called a beard, that is retained along its length by a locking comb. The unclamped end of the beard is inserted into a length/strength device that measures the various lengths of the fibers in the beard. A pair of jaws clamp the beard and slowly separate from each other until the fibers break. The length measurement is recorded, and the force required to break the beard is recorded. These physical properties, in combination with other measured properties, are used to classify the fibers.

What is needed, therefore, is a system for preparing the fibers prior to testing.

SUMMARY OF THE CLAIMS

These needs are met by a fiber sample conditioning system having a comb for engaging and retaining fibers to form a beard and at least two rotating brushes for brushing the fibers simultaneously from opposite sides of the beard in a direction along the fibers away from the comb.

By brushing the fibers of the beard between two opposing rotating brushes, a high degree of singulation and linearization occurs in the fibers of the beard, which enhances the results of subsequent testing.

In various embodiments according to this aspect of the invention, the fibers are cotton fibers, synthetic staple fibers, or a blend of both. In some embodiments two combs in parallel retain fibers simultaneously to form two beards, and two sets of two brushes each simultaneously brush the two beards.

According to another aspect of the invention there is described a fiber sample testing system having a drum for presenting fiber tufts protruding through a peripheral wall of the drum, a first translator for moving a comb toward the drum, the comb for engaging and retaining fibers from the fiber tufts to form a beard, the first translator for moving the comb away from the drum, a second translator for simultaneously moving at least two rotating brushes toward the beard from opposite sides of the beard, the brushes for brushing the beard in a direction along the fibers away from the comb, the first translator for moving the beard out from between the brushes, a third translator for moving the comb to a testing station, the first translator for moving the beard into the testing station, and the testing station for testing the fibers in the beard.

In various embodiments according to this aspect of the invention, the fibers are cotton fibers, synthetic fibers, or a blend of both. In some embodiments two combs retain fibers from two drums simultaneously to form two beards, two sets of two brushes simultaneously brush the two beards, and two testing stations simultaneously test the fibers in the two beards. In some embodiments the testing station is a combined fiber length and fiber strength testing station.

According to yet another aspect of the invention there is described a method of conditioning fibers by forming a beard of the fibers within a test plane, bringing at least two opposing and rotating brushes into the test plane from opposite sides of the test plane and against the beard, and brushing the beard along the test plane between the at least two opposing brushes to substantially singulate and linearize the fibers of the beard.

In various embodiments according to this aspect of the invention, the step of forming the beard includes moving a comb within the test plane to engage and withdraw the fibers from fiber tufts that are protruding through a peripheral wall of a rotating drum. Some embodiments include testing the singulated and linearized beard within the test plane for length and strength of fibers. In some embodiments the fibers are cotton fibers. In some embodiments two beards are formed simultaneously, and two sets of two brushes simultaneously brush the two beards.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
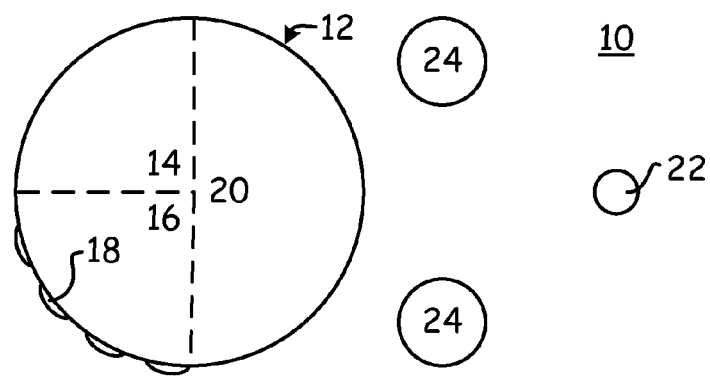
FIG. 1 is a diagrammatic view of a fiber sample forming and conditioning apparatus in an initial position according to an embodiment of the present invention. The view is from the ends of the shafts of the sample drum and brushes in a direction parallel to the shafts.

With reference now to FIG. 1, there is depicted a diagrammatic view in a direction parallel to the shafts of the drum 12 and brushes 24, of a fiber sample forming and conditioning apparatus 10 in an initial position according to an embodiment of the present invention. In this embodiment a drum 12 is loaded with the fiber sample. However, it is appreciated that a variety of different fiber sampling methods are contemplated herein. In the embodiment depicted, the drum 12 is divided into three major zones. Zone 14 is an opening along the peripheral wall of the drum 12, into which a fiber sample is placed. Zone 16 has apertures formed in the peripheral wall of the drum 12, through which tufts 18 of the fiber sample protrude, and a sample hand that presses the fiber sample against the peripheral wall and through the apertures to form the tufts 18.

Figure 2:
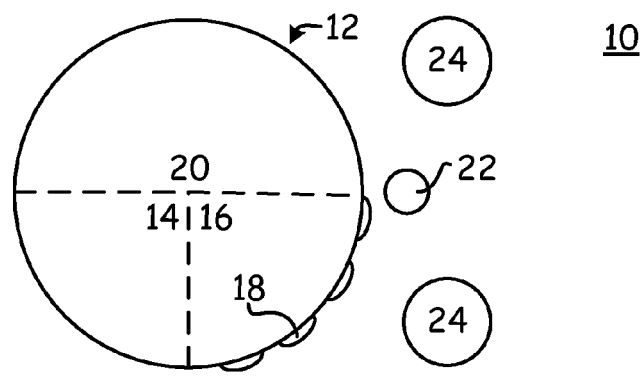
FIG. 2 is a diagrammatic view of a fiber sample forming and conditioning apparatus in a capture position according to an embodiment of the present invention.
Figure 3:
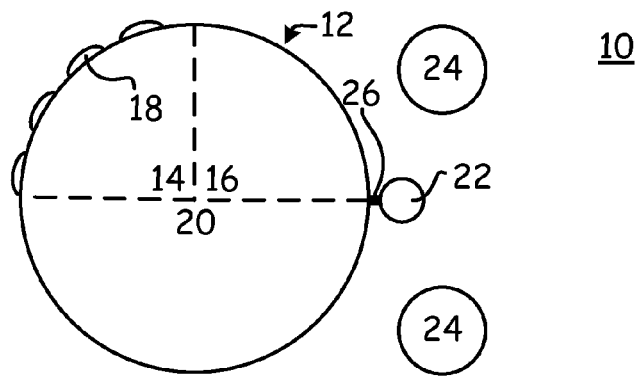
FIG. 3 is a diagrammatic view of a fiber sample forming and conditioning apparatus in a carding position according to an embodiment of the present invention.

The drum 12 is loaded with a fiber sample, and begins to rotate. A comb 22 is brought into proximity with the peripheral wall of the drum 12 (as depicted in FIG. 2), such that teeth in an open position on the comb 22 (not depicted so as to not unnecessarily encumber the drawings) can engage the fiber tufts 18 and capture and withdraw fibers of the fiber sample as the tufts 18 rotate past the comb 22. After the drum 12 rotates the tufts 18 past the comb 22, the teeth of the comb 22 are moved to a closed position so as to retain the withdrawn fibers, in a configuration that is referred to as a beard 26. With the teeth in the closed position, the drum 12 rotates to another zone 20 (as depicted in FIG. 3) where carding pins are disposed on the peripheral wall of the drum 12, which card the beard 26.

Figure 4:
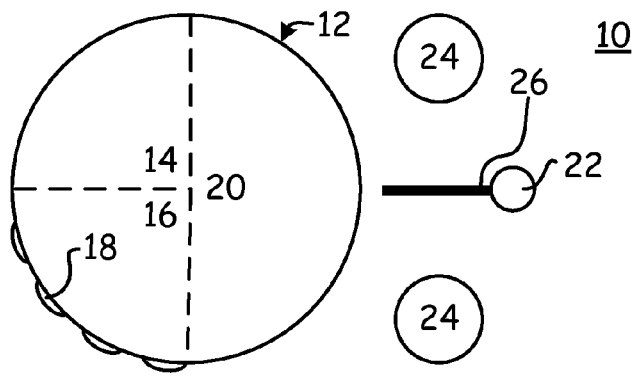
FIG. 4 is a diagrammatic view of a fiber sample forming and conditioning apparatus in a first withdraw position according to an embodiment of the present invention.
Figure 5:
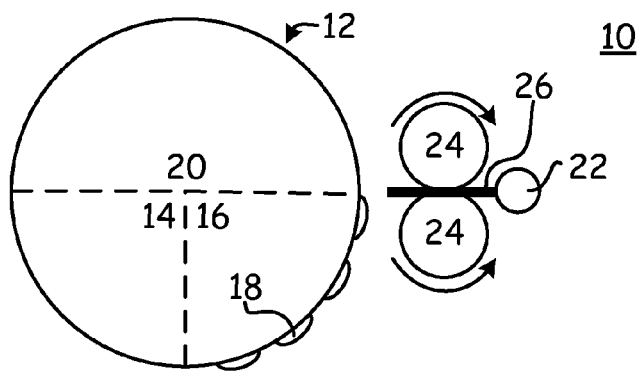
FIG. 5 is a diagrammatic view of a fiber sample forming and conditioning apparatus in a brushing position according to an embodiment of the present invention.
Figure 6:
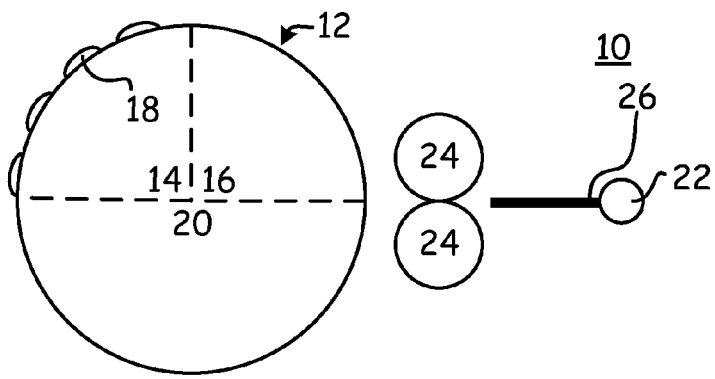
FIG. 6 is a diagrammatic view of a fiber sample forming and conditioning apparatus in a second withdraw position according to an embodiment of the present invention.

The comb 22 is retracted from the drum 12, so that the beard 26 no longer engages the drum 12 (as depicted in FIG. 4), and two opposing brushes 24 are brought into contact with the beard 26 from opposite sides (as depicted in FIG. 5). The brushes 24 are rotating such that the direction of the bristles of the brushes 24 where they contact the beard 26 are brushing away from the comb 22 and toward the drum 12. The brushes 24 might only contact and brush a portion of the length of the beard 26, or in other embodiments, might start by brushing the initial portion of the beard 26 that is retained by the teeth of the comb 22, and then brush the entire length of the beard 26, such as by continuing to withdraw the comb 26 (as depicted in FIG. 6). Brushing in this manner removes tangles between the fibers of the beard 26, and generally singulates and linearizes the fibers of the beard 26.

Translators can be used to provide the linear movement of the various elements as described herein. The translators are not depicted in the various views, so as to not unnecessarily encumber the drawings with details that are more easily understood. For example, the various elements can be mounted on tracks and mobilized using air pistons, lead screws, stepper motors, or other means as understood in the art. Rotational movements can be accomplished by direct motors, belted motors, or other means as understood in the art. All aspects of the systems as described herein are in one embodiment controlled by a digital programmable controller, such as a personal computer or the like.

Figure 7:
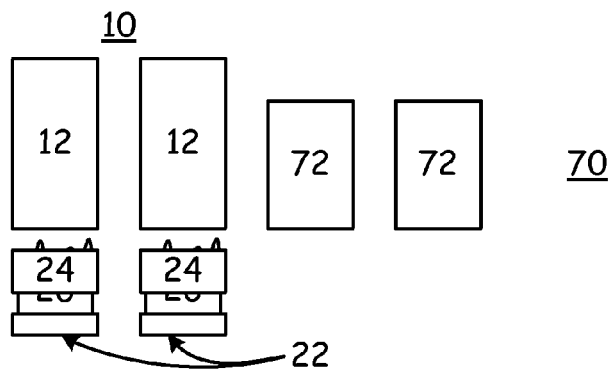
FIG. 7 is a first diagrammatic view of a fiber sample testing apparatus including multiple instances of the forming and conditioning apparatus and testing stations.
Figure 8:
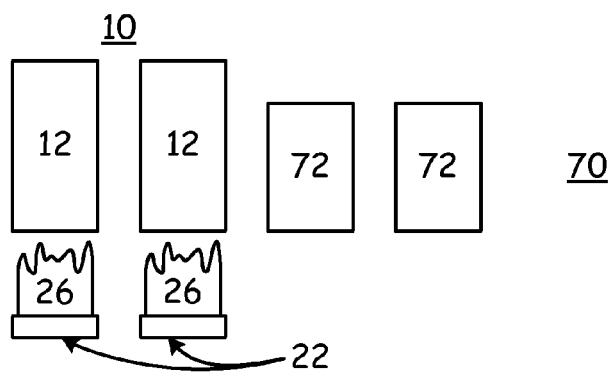
FIG. 8 is a second diagrammatic view of a fiber sample testing apparatus including multiple instances of the forming and conditioning apparatus and testing stations.
Figure 9:
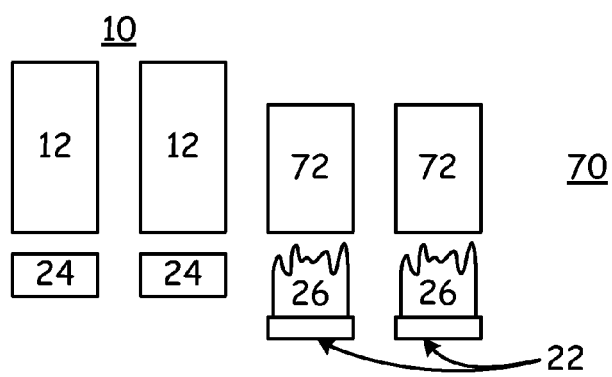
FIG. 9 is a third diagrammatic view of a fiber sample testing apparatus including multiple instances of the forming and conditioning apparatus and testing stations.
Figure 10:
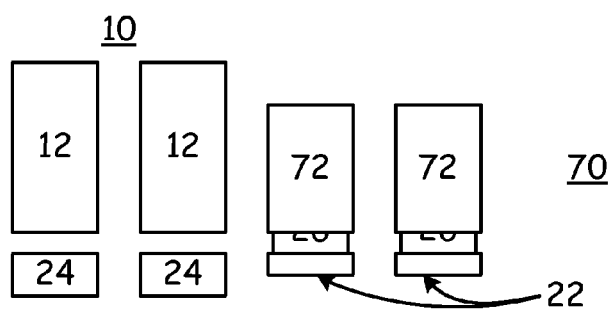
FIG. 10 is a fourth diagrammatic view of a fiber sample testing apparatus including multiple instances of the forming and conditioning apparatus and testing stations.

FIG. 7 depicts a top plan diagrammatic view of a fiber testing station 70, including two instances of the fiber sampling and conditioning stations 10. In this embodiment, two drums 12 are disposed side by side, and two combs 22 retrieve fiber samples from the drums 12, either independently or simultaneously. Two sets of brushes 24 condition the beard 26 as it is withdrawn by the combs 22. FIG. 8 depicts the apparatus 70 with the brushes 24 removed, so as to show the beards 26 that are formed and brushed. As depicted in FIG. 9, the combs 22 are moved to a second position of the apparatus 70, where testing devices 72, such as length and strength testers, are disposed and stand ready to perform tests on the fibers of the beards 26. In FIG. 10, the combs 22 have been moved so as to permit the beards 26 to be drawn into the testing devices 72, such as by a vacuum air flow, so as to be tested. It is appreciated that in other embodiments only one conditioning apparatus 10 is provided and only one tester 72 is provided, and in other embodiments more than two conditioning apparatuses 10 are provide and more than two testers 72 are provided.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A fiber sample conditioning system, comprising:
   a comb for engaging and retaining fibers to form a beard, and
   at least two rotating brushes for brushing the fibers simultaneously from opposite sides of the beard in a direction along the fibers away from the comb.

2. The fiber sample conditioning system of claim 1, wherein the fibers are at least one of cotton fibers and synthetic staple fibers.

3. The fiber sample conditioning system of claim 1, wherein two combs retain fibers simultaneously to form two beards, and two sets of two brushes simultaneously brush the two beards.

4. A fiber sample testing system, comprising:
   a drum for presenting fiber tufts protruding through a peripheral wall of the drum,
   a first translator for moving a comb toward the drum,
   the comb for engaging and retaining fibers from the fiber tufts to form a beard,
   the first translator for moving the comb away from the drum,
   a second translator for simultaneously moving at least two rotating brushes toward the beard from opposite sides of the beard,
   the brushes for brushing the beard in a direction along the fibers away from the comb,
   the first translator for moving the beard out from between the brushes,
   a third translator for moving the comb to a testing station,
   the first translator for moving the beard into the testing station, and
   the testing station for testing the fibers in the beard.

5. The fiber sample testing system of claim 4, wherein the fibers are at least one of cotton fibers and synthetic staple fibers.

6. The fiber sample testing system of claim 4, wherein two combs retain fibers from two drums simultaneously to form two beards, and two sets of two brushes simultaneously brush the two beards, and two testing stations simultaneously test the fibers in the two beards.

7. The fiber sample testing system of claim 4, wherein the testing station is a combined fiber length and fiber strength testing station.

8. A method of conditioning fibers, the method comprising the steps of:
   forming a beard of the fibers within a test plane, bringing at least two opposing and rotating brushes into the test plane from opposite sides of the test plane and against the beard, and brushing the beard along the test plane between the at least two opposing brushes to substantially singulate and linearize the fibers of the beard.

9. The method of claim 8, wherein the step of forming the beard comprises moving a comb within the test plane to engage and withdraw the fibers from fiber tufts that are protruding through a peripheral wall of a rotating drum.

10. The method of claim 8, further comprising testing the singulated and linearized beard within the test plane for length and strength of fibers.

11. The method of claim 8, wherein the fibers are at least one of cotton fibers and synthetic staple fibers.

12. The method of claim 8, wherein two beards are formed simultaneously, and two sets of two brushes simultaneously brush the two beards.

* * * * *